(12) United States Patent
Tseng et al.

(10) Patent No.: US 10,753,917 B2
(45) Date of Patent: Aug. 25, 2020

(54) HYDROGEN SENSING DEVICE

(71) Applicant: NATIONAL CHIAO TUNG UNIVERSITY, Hsinchu (TW)

(72) Inventors: Yuan-Chieh Tseng, Hsinchu (TW); Jaw-Yeu Liang, Hsinchu (TW); Yun-Chieh Pai, Hsinchu (TW); Yu-Jung Chou, Hsinchu (TW); Wen-Chin Lin, Hsinchu (TW); Chih-Huang Lai, Hsinchu (TW)

(73) Assignee: NATIONAL CHIAO TUNG UNIVERSITY, Hsinchu (TW)

( * ) Notice: Subject to any disclaimer, the term of this patent is extended or adjusted under 35 U.S.C. 154(b) by 182 days.

(21) Appl. No.: 15/977,629

(22) Filed: May 11, 2018

(65) Prior Publication Data

US 2018/0328902 A1 Nov. 15, 2018

(30) Foreign Application Priority Data

May 12, 2017 (TW) .............................. 106115749 A

(51) Int. Cl.
| | |
|---|---|
| *G01N 33/00* | (2006.01) |
| *G01N 31/22* | (2006.01) |
| *G01N 27/12* | (2006.01) |
| *G01N 33/20* | (2019.01) |

(52) U.S. Cl.
CPC .......... *G01N 33/005* (2013.01); *G01N 27/12* (2013.01); *G01N 31/22* (2013.01); *G01N 33/0059* (2013.01); *G01N 33/20* (2013.01)

(58) Field of Classification Search
None
See application file for complete search history.

(56) References Cited

U.S. PATENT DOCUMENTS

| | | | |
|---|---|---|---|
| 6,773,515 B2* | 8/2004 | Li | B32B 15/01 148/240 |
| 9,097,677 B1* | 8/2015 | Miller | G01N 27/74 |
| 2012/0131988 A1* | 5/2012 | Schmid | G01N 27/74 73/25.02 |

FOREIGN PATENT DOCUMENTS

| | | |
|---|---|---|
| TW | 385366 B | 3/2000 |
| TW | 444255 B | 7/2001 |
| TW | 447004 B | 7/2001 |
| TW | 573120 B | 1/2004 |
| TW | 586007 B | 5/2004 |
| TW | 591226 B | 6/2004 |
| TW | 200841012 A | 10/2008 |
| TW | I303310 B | 11/2008 |
| TW | I311199 B | 6/2009 |

(Continued)

OTHER PUBLICATIONS

Crosby S. Chang, et al., "Metallic spintronic thin film as a hydrogen sensor," Applied Physics Letters, 102, 142405 (2013), total 6 pages.

(Continued)

*Primary Examiner* — Paul M. West
*Assistant Examiner* — Mark A Shabman

(57) ABSTRACT

A hydrogen sensing device includes a multi-layered structure member. The multi-layered structure member includes a stack of alternatingly disposed magnetic layers and non-ferromagnetic layers. One of the magnetic layers is a topmost layer of the multi-layered structure member. The topmost layer includes a palladium-based material to detect hydrogen.

9 Claims, 5 Drawing Sheets

(56) References Cited

FOREIGN PATENT DOCUMENTS

| TW | 200951432 A | 12/2009 |
|---|---|---|
| TW | I351761 B | 11/2011 |
| TW | I384562 B1 | 2/2013 |
| TW | I429090 B | 3/2014 |
| TW | I443332 B | 7/2014 |
| TW | 201616125 A | 5/2016 |

OTHER PUBLICATIONS

S. Akamaru, et al., "Sensing hydrogen in the gas phase using ferromagnetic Pd—Co films," Journal of Alloys and Compounds, 645 (2015), pp. S213-S216.

W.-C.Lin, et al., "Hydrogenation induced reversible modulation of perpendicular magnetic coercivity in Pd/Co/Pd films," Appl. Phys. Lett. 102, 252404 (2013), total 6 pages.

W.-C.Lin, et al, "Hydrogen absorption-induced reversible change in magnetic properties of Co—Pd alloy films," Journal of Alloys and Compounds 661 (2016), pp. 20-26.

\* cited by examiner

HYDROGEN SENSING DEVICE

CROSS-REFERENCE TO RELATED APPLICATION

This application claims priority of Taiwanese Invention Patent Application No. 106115749, filed on May 12, 2017.

FIELD

The disclosure relates to a hydrogen sensing device, and more particularly to a hydrogen sensing device including a magnetic layer for detecting hydrogen.

BACKGROUND

Since hydrogen is highly flammable, a hydrogen sensing device is required to be disposed in a room or place with hydrogen exposure for sensing hydrogen leakage.

Conventional hydrogen sensing devices are mainly classified as optical fiber-based hydrogen sensing devices, electrochemistry-based hydrogen sensing devices, and Schottky diode-based hydrogen sensing devices. There is still a need in the art to provide a hydrogen sensing device with improved sensitivity in sensing hydrogen.

SUMMARY

Therefore, an object of the disclosure is to provide a hydrogen sensing device that can alleviate at least one of the drawbacks of the prior art.

According to the disclosure, the hydrogen sensing device includes a multi-layered structure member.

The multi-layered structure member includes a stack of alternatingly disposed magnetic layers and non-ferromagnetic layers. One of the magnetic layers is a topmost layer of the multi-layered structure member. The topmost layer includes a palladium-based material to detect hydrogen.

BRIEF DESCRIPTION OF THE DRAWINGS

Other features and advantages of the disclosure will become apparent in the following detailed description of the embodiment with reference to the accompanying drawings, of which.

DETAILED DESCRIPTION

Figure 1:
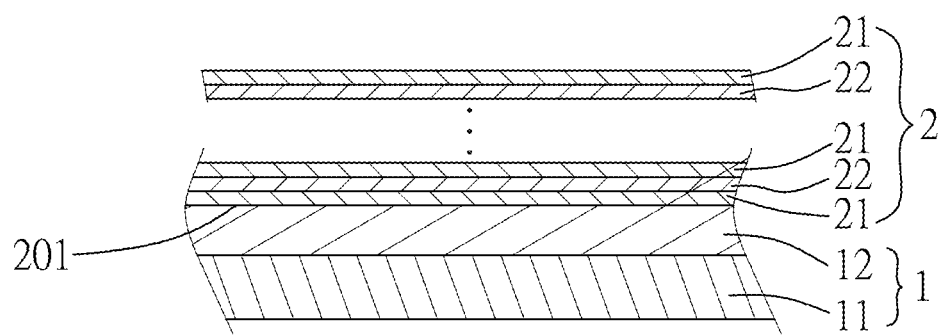
FIG. 1 is a fragmentary schematic sectional view illustrating an embodiment of a hydrogen sensing device according to the disclosure.

Referring to FIG. 1, an embodiment of a hydrogen sensing device according to the disclosure includes a substrate 11, a seed layer 12, and a multi-layered structure member 2.

The substrate 11 is connected to a bottom surface 201 of the multi-layered structure member 2, and the seed layer 12 is formed between the substrate 11 and the bottom surface 201 of the multi-layered structure member 2.

The multi-layered structure member 2 includes a stack of magnetic layers 21 and non-ferromagnetic layers 22 disposed alternatingly. One of the magnetic layers 21 is a topmost layer of the multi-layered structure member 2. The topmost layer of the magnetic layers 21 is opposite to the substrate 11 and includes a palladium-based material to detect hydrogen.

In the embodiment, the hydrogen sensing device is manufactured in a vacuum chamber at a pressure of $10^{-7}$ Torr using magnetron sputtering techniques. The seed layer 12 is first formed on the substrate 11 and then the multi-layered structure member 2 is formed on the seed layer 12. Formation of the seed layer 12 facilitates homogeneous growth of one of the magnetic and non-ferromagnetic layers 21, 22 of the multi-layered structure member 2 thereon, subsequently forming a stable stacking of the remainder of the magnetic and non-ferromagnetic layers 21, 22, thereby improving the bonding strength among interfaces of the magnetic layers 21 and the non-ferromagnetic layers 22. In this embodiment, each of the magnetic layers 21 of the multi-layered structure member 2 includes the palladium-based material. For example, the palladium-based material includes a palladium-cobalt alloy. To be specific, the layer formed directly on the seed layer 12 is one of the magnetic layers 21. Each of the magnetic layers 21 may be made from the palladium-cobalt alloy including 50% to 95% of palladium and a balance of cobalt. In the embodiment, the substrate 11 is a monocrystalline silicon (Si) wafer having a (100) crystal plane, the seed layer 12 includes iron, each of the magnetic layers 21 is made from the palladium-cobalt alloy including 60% of palladium and 40% of cobalt, and each of the non-ferromagnetic layers 22 is made from copper (Cu). Alternatively, the substrate 11 may be made from another material, such as glass, as long as deposition of the seed layer 12 or the multi-layered structure member 2 is allowable. Besides, hydrogen sensing is substantially performed by the topmost layer of the multi-layered structure member 2 (e.g., the topmost layer of the magnetic layers 21) and will not be affected by the substrate 11. Hence, substrate 11 is optional for the hydrogen sensing device of the disclosure. In one form, the magnetic layers 21 of the multi-layered structure member 2 may be free of palladium, excluding the topmost layer of the magnetic layers 21. In another form, the magnetic layers 21 of the multi-layered structure member 2 may be made from any other magnetic transition metals, and the non-ferromagnetic layers 22 of the multi-layered structure member 2 may include non-ferromagnetic materials selected from the group consisting of copper (Cu), silver (Ag), gold (Au), chromium (Cr), aluminum (Al), tantalum (Ta), and alloys thereof. In one form, the non-ferromagnetic layers 22 of the multi-layered structure member 2 may include the non-ferromagnetic materials selected from the group consisting of copper (Cu), silver (Ag), gold (Au), chromium (Cr), aluminum (Al), tantalum (Ta), ruthenium (Ru), platinum (Pt), and alloys thereof. Since the multi-layered structure member 2 is connected to the Si wafer, the hydrogen sensing device of the disclosure is compatible with other devices that are formed on the Si wafer. Thus, the hydrogen sensing device of the disclosure and other devices can be integrated on the Si wafer using system-on-chip techniques for enhancing quality and efficiency of signal processing and data transmission of the integrated devices therefrom.

In this embodiment, the seed layer 12 has a thickness of 7 nm, the multi-layered structure member 2 has a total number of 11 layers, and each of the magnetic layers 21 and the non-ferromagnetic layers 22 has a thickness of 2 nm.

Since the increase in the total number of the magnetic layers 21 and the non-ferromagnetic layers 22 of the multi-layered structure member 2 will enhance the magnetoresistance (MR) effect of the multi-layered structure member 2, for inducing the giant magnetoresistance (GMR) effect, the total number of the magnetic layers 21 and the non-ferromagnetic layers 22 may be adjusted to range from 3 to 50, and the thickness of each of the magnetic layers 21 and the non-ferromagnetic layers 22 may be adjusted to range from 0.5 nm to 5 nm according to Ruderman-Kittel-Kasuya-Yosida (RKKY) interaction.

In the following, magnetoresistance values of a sample of this embodiment of the hydrogen sensing device according to the disclosure are measured by a self-made testing system, which is based on the magneto-optical Kerr effect (MOKE). The system includes a chamber for disposing the sample, and a pressure of a hydrogen gas introduced into the chamber is controllable. The system further includes a four point probe measuring device that is disposed in the chamber for measuring an electrical resistance of the sample, and an electromagnet that is configured to apply magnetic field ranging from −3000 Oe to 3000 Oe to the sample. The electrical resistance of the sample is measured by the measuring device under different hydrogen pressures in different applied magnetic fields.

Figure 2:
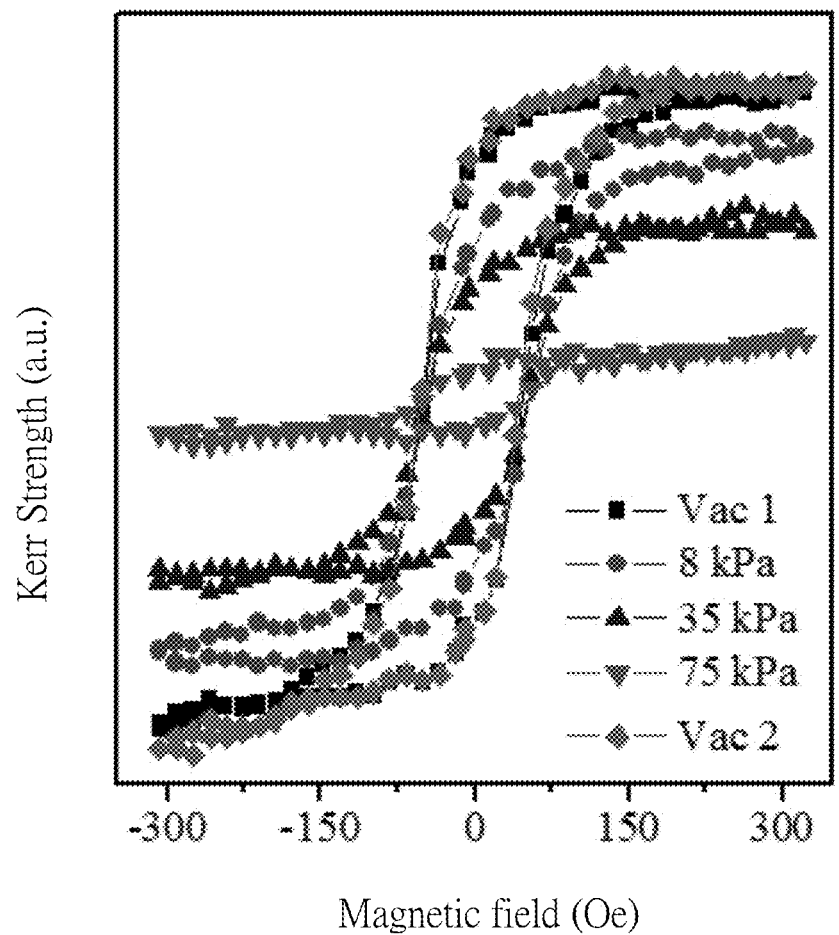
FIG. 2 is a plot showing hysteresis curves of a sample of the embodiment under different hydrogen pressures.

FIG. 2 is a plot illustrating hysteresis curves of a sample under different hydrogen pressures. A hysteresis curve (Vac $1^{st}$) composed of data represented by square marks (-■-) is obtained under an initial vacuum condition, where hydrogen gas is yet to be introduced into the chamber. A hysteresis curve (Vac $2^{nd}$) composed of data represented by diamond marks (-♦-) is obtained under a final vacuum condition where the hydrogen gas that is introduced into the chamber has been removed. Hysteresis curves composed of data represented by circle marks (-●-), triangle marks (-▲-), and inverted-triangle marks (-▼-) are respectively obtained under the hydrogen pressures of 8 kPa, 35 kPa and 75 kPa, in the chamber. The results show that the saturation magnetization of the sample will be reduced with an increase in the hydrogen pressure in the chamber. The results further indicate that saturation magnetization of the sample is reversible under different hydrogen pressures.

Figure 3:
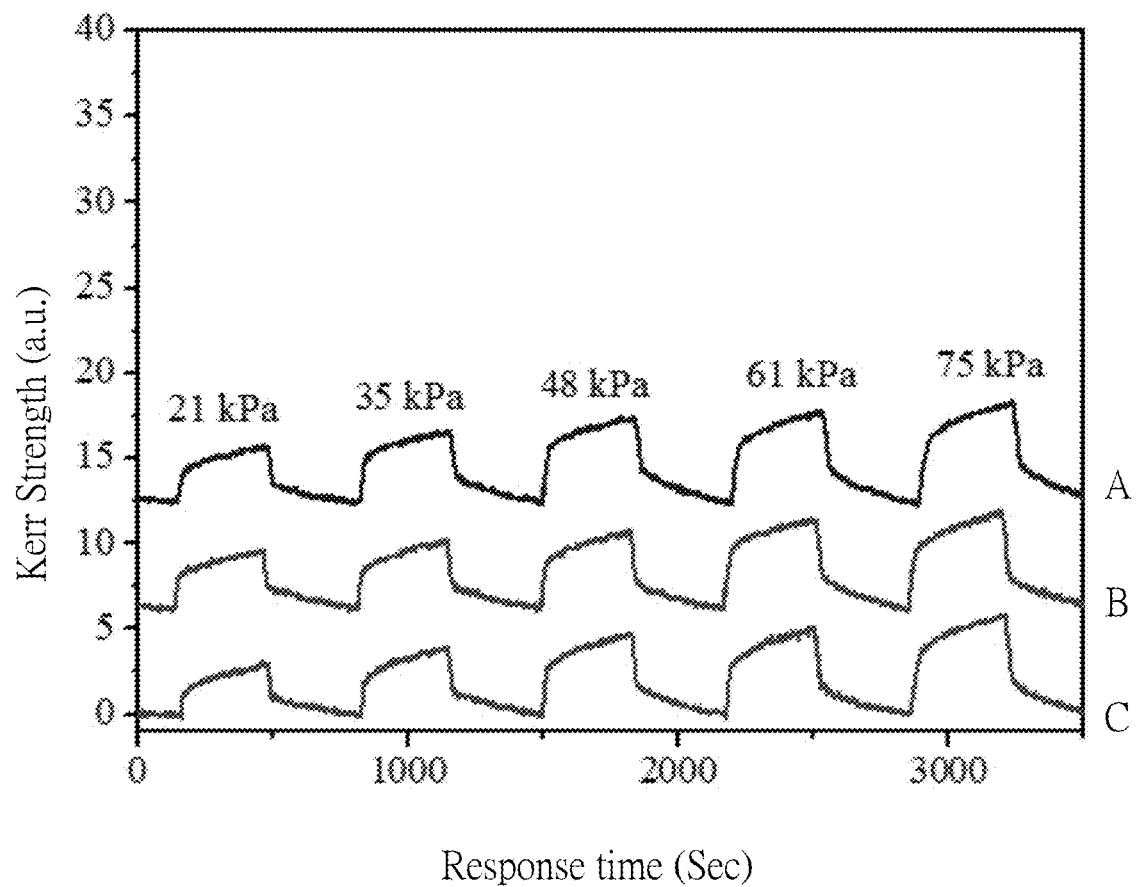
FIGS. 3 and 4 are plots of electrical resistance variation versus response time of the sample measured at different applied magnetic fields under different hydrogen pressures.
Figure 4:
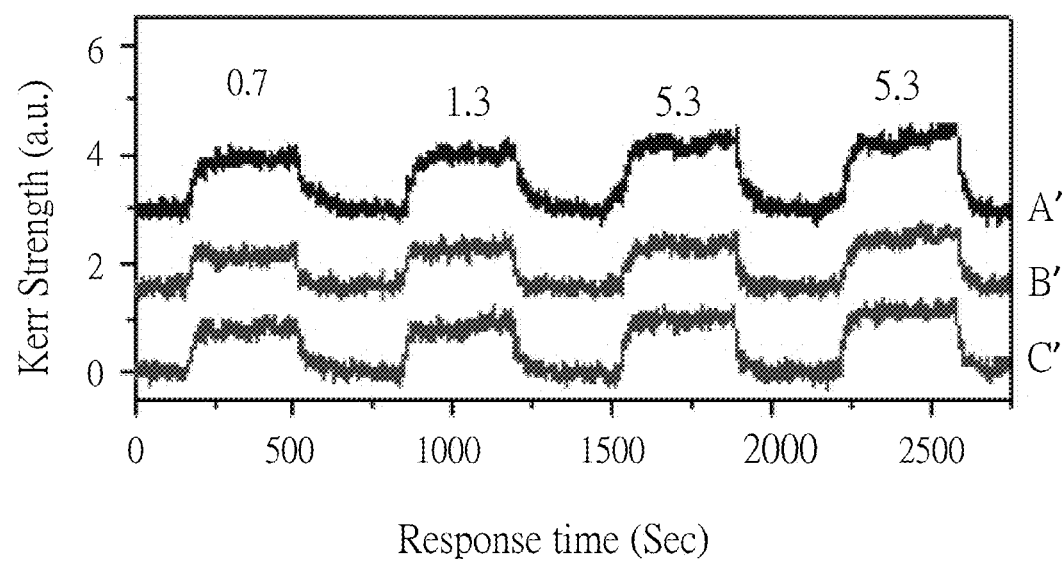

FIGS. 3 and 4 are plots of electrical resistance variation (ΔR) of the sample versus response time in different applied magnetic fields under different hydrogen pressures. More specifically, curves A, B and C of the plot of FIG. 3 are respectively obtained from applied magnetic fields of 0, 50 and 1000 Oe. Likewise, curves A', B' and C' of the plot of FIG. 4 are respectively obtained from applied magnetic fields of 0, 50 and 1000 Oe. Peaks of each of the curves A, B and C in FIG. 3 represent that the sample is subjected to pulsed hydrogen pressures of 21 kPa, 35 kPa, 48 kPa, 61 kPa and 75 kPa in the chamber, and peaks of each of the curves A', B' and C' in FIG. 4 represent that the sample is subjected to pulsed hydrogen pressures of 0.7 kPa, 1.3 kPa, 2.7 kPa and 5.3 kPa in the chamber. Troughs of the curves A, B, C, A', B', C' in both FIGS. 3 and 4 represent that the sample is not exposed to an atmosphere containing hydrogen gas (i.e., the chamber is vacuumed).

In FIGS. 3 and 4, the ΔR of the sample in each of the applied magnetic fields of 50 and 1000 Oe is a value obtained by subtracting the initial electrical resistance of the sample in the initial vacuum chamber from the electrical resistance of the sample measured under the condition that the sample is subjected to the respective pulsed hydrogen pressures. The results indicate that, since palladium hydride has an electrical resistance higher than that of palladium, the ΔR of the sample will increase significantly following exposure to the hydrogen atmosphere, while the ΔR will decrease with the decrease in the hydrogen pressure. Besides, the ΔR of the sample which is brought into contact with the hydrogen gas in the higher applied magnetic field is greater compared to that of the sample which is brought into contact with the hydrogen gas in the lower applied magnetic field. Hence, the results of FIGS. 3 and 4 demonstrate that the sensing device of the disclosure is able to respond to the presence of the hydrogen gas in a quick and reproducible manner under the applied magnetic fields.

Figure 5:
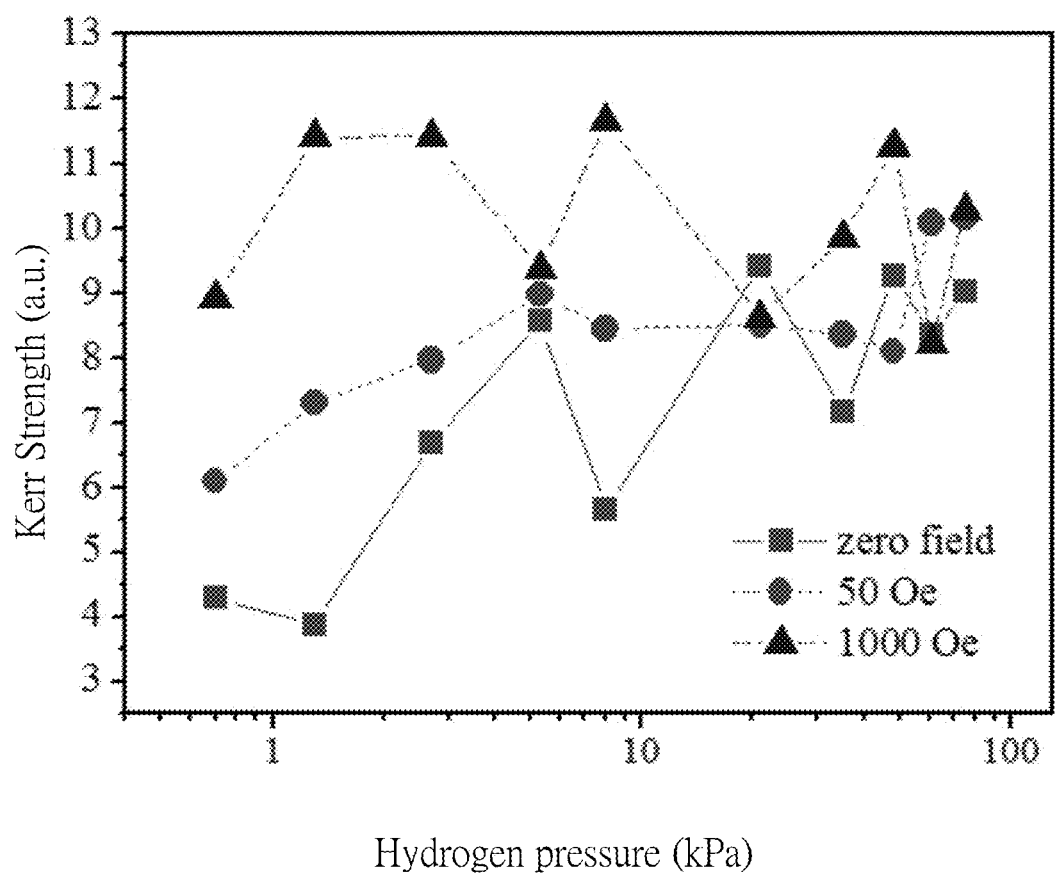
FIG. 5 is a plot of signal-to-noise ratio versus hydrogen pressure of the sample under different hydrogen pressures.

A signal-to-noise ratio (SNR, $\Delta R_{avg}/\sigma_m$) is defined to quantize sensitivity of the sample of the hydrogen sensing device of the disclosure, where the $\Delta R_{avg}$ is an average value of the ΔR of the sample measured five times, and the $\sigma_n$ is a standard deviation of the ΔR values. FIG. 5 is a plot showing the SNR of the sample under different hydrogen pressures. A curve composed of data represented by square marks (-■-) illustrates the SNR of the sample measured in the applied magnetic field of 0 Oe, a curve composed of data represented by circle marks (-●-) illustrates the SNR of the sample measured in the applied magnetic field of 50 Oe, and a curve composed of data represented by triangle marks (-▲-) illustrates the SNR of the example measured in the applied magnetic field of 1000 Oe. The results show that the SNR of the sample is increased with an increase in magnetic field strength. Furthermore, the SNR of the sample is increased at an atmosphere with relatively low hydrogen pressure and under relatively high applied magnetic field. In other words, the sensitivity in sensing hydrogen of the hydrogen sensing device of the disclosure in a relatively low hydrogen atmosphere can be increased by applying a relatively high magnetic field.

To sum up, by virtue of the design and the material of the multi-layered structure member 2, the sensitivity in sensing hydrogen of the hydrogen sensing device of the disclosure is improved.

In the description above, for the purposes of explanation, numerous specific details have been set forth in order to provide a thorough understanding of the embodiment. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects.

While the disclosure has been described in connection with what is considered the exemplary embodiment, it is understood, that this disclosure is not limited to the disclosed embodiment but is intended to cover various arrangements included within the spirit and scope of the broadest interpretation so as to encompass all such modifications and equivalent arrangements.

What is claimed is:
1. A hydrogen sensing device, comprising:
a multi-layered structure member including a stack, of alternatingly disposed magnetic layers and non-ferromagnetic layers,
wherein one of said magnetic layers is a topmost layer of said multi-layered structure member; and wherein said topmost layer includes a palladium-based material to detect hydrogen; and wherein the palladium-based material includes a palladium-based alloy that includes 50% to 95% of palladium and a balance of cobalt.

2. The hydrogen sensing device of claim 1, wherein each of said magnetic layers includes the palladium-based material.

3. The hydrogen sensing device of claim 1, wherein said non-ferromagnetic layers include a non-ferromagnetic material selected from the group consisting of copper (Cu), silver (Ag), gold (Au), chromium (Cr), aluminum (Al), tantalum (Ta) and alloys thereof.

4. The hydrogen sensing device of claim 3, wherein the non-ferromagnetic material includes Cu.

5. The hydrogen sensing device of claim 1, wherein each of said magnetic layers and said non-ferromagnetic layers has a thickness ranging from 0.5 nm to 5 nm.

6. The hydrogen sensing device of claim 1, wherein a total number of said magnetic layers and said non-ferromagnetic layers ranges from 3 to 50.

7. The hydrogen sensing device of claim 1, further comprising a substrate that is connected to a bottom surface of said multi-layered structure member opposite to said topmost layer.

8. The hydrogen sensing device of claim 7, further comprising a seed layer formed between said substrate and said bottom surface of said multi-layered structure member.

9. The hydrogen sensing device of claim 8, wherein said seed layer includes iron.

* * * * *